United States Patent [19]
Cornell et al.

[11] Patent Number: 4,632,975
[45] Date of Patent: Dec. 30, 1986

[54] POLYFUNCTIONAL ACRYLATE DERIVATIVES OF CAPROLACTONE-POLYOLS

[75] Inventors: John A. Cornell, West Chester, Pa.; Steven J. Kubisen, Jr., North Brunswick, N.J.

[73] Assignee: Union Carbide Corporation, Danbury, Conn.

[21] Appl. No.: 777,870

[22] Filed: Sep. 19, 1985

Related U.S. Application Data

[63] Continuation of Ser. No. 578,423, Feb. 9, 1984, abandoned.

[51] Int. Cl.$^4$ .............................................. C08G 63/76
[52] U.S. Cl. .................................... 528/354; 560/183

[58] Field of Search ...................... 528/354; 525/411; 560/183

[56] References Cited

U.S. PATENT DOCUMENTS 3,700,643 10/1972 Smith et al. ................ 260/77.5 AN
4,281,172 7/1981 Knopf .................................. 528/354

Primary Examiner—Earl Nielsen
Attorney, Agent, or Firm—Jean B. Mauro

[57] ABSTRACT

Described herein are polyfunctional acrylate derivatives of caprolactone-polyols. The derivatives have low viscosity, are thermally stable and impart toughness properties to radiation cured coatings utilizing them.

5 Claims, No Drawings

POLYFUNCTIONAL ACRYLATE DERIVATIVES OF CAPROLACTONE-POLYOLS

This application is a continuation of prior U.S. application Ser. No. 578,423, filed Feb. 9, 1984, now abandoned.

BACKGROUND OF THE INVENTION

This invention is directed to polyfunctional acrylate derivatives of caprolactone-polyols.

Polyfunctional acrylates have been used in a large number of fields including coating and elastomers. Most ultraviolet (UV) light applications are based on binders containing acrylic unsaturations. These binders are generally classified as epoxy acrylates, urethane acrylates and polyester acrylates. Glycol acrylates are also extensively used to modify UV curing systems.

Acrylate-capped polycaprolactone polyol derivatives are described in U.S. Pat. No. 3,700,643. The derivatives are described as useful in producing coating compostions that are readily cured to solid protective films. The acrylate-capped polycaprolactone compounds include those defined by the following formula:

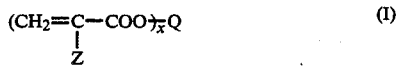

where Z is hydrogen or methyl, Q is the residue remaining after reaction of the caprolactone polyol and x is an integer having a value of from 1 to 4. In columns 6 and 7 the patent describes the production of mono-hydroxyl mono-acrylate-capped polycaprolactone and diacrylate capped polucaprolactone, i.e., when x in the above formula is 1 or 2. However, the acrylate-capped polycaprolactone compounds of U.S. Pat. No. 3,700,643 have high viscosity and reduced compatibility with several types of polymers. Accordingly, they have limited utility in coatings formulations.

The process employed in U.S. Pat. No. 3,700,643 produces acrylate-capped polycaprolactones which are high in viscosity, which limits their use as diluents. The process of U.S. Pat. No. 3,700,643 is conducted under a nitrogen atmosphere at elevated temperatures. When this process was repeated, gels formed due to polymerization of the acrylic acid and the acrylates which are used. In a commercial process, the excess acrylic acid is preferably removed by water washing. Using the conditions described in U.S. Pat. No. 3,700,643 emulsions formed when water was added to the reaction mixture, due to the presence of polyacrylic acid. Further, the solvent in the products from U.S. Pat. No. 3,700,643 (Example 13) was stripped off in an inert atmosphere causing an additional increase in viscosity. Finally, the process of U.S. Pat. No. 3,700,643 employs a high level of the inhibitor, phenothiazine, which remains in the product. Phenothiazine at the levels used in Example 13 would interefere with photochemical curing procedures because of the high molar absorptivity of phenothiazine.

The polyfunctional acrylate derivatives of this invention have generally lower viscosity, are thermally stable and impart toughness properties to compositions utilizing them. In particular, they are useful as polyurethane modifiers. Also, they are compatible with a number of polymers and when polymerized, improve the flexibility and toughness of the polymer. Prior art polyester polyols are high in viscosity. For example, an acrylated polyester VPS-2700 manufactured by Degussa Corporation for general radiation cured coatings has a viscosity of 8,000 to 13,000 centipoise. In addition, they are difficult to manufacture in functionalities of three or greater since the use of trifunctional monomers in polyesters lead to network structures and gels.

THE INVENTION

The polyfunctional acrylate derivatives of caprolactone-polyol are characterized by the following formula:

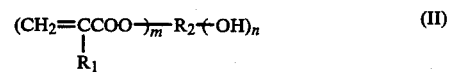

wherein $R_1$ is hydrogen or methyl, $R_2$ is the residue remaining after reaction of caprolactone monomer with an organic functional initiator which can be any polyhydroxyl compound as shown in U.S. Pat. No. 3,169,545, m is an integer of 2 to 6, and n is an integer of 0 to 2, with the proviso that m+n is greater than or equal to 3, and m is greater than n.

The caprolactone polyols that can be used to prepare the polyfunctional acrylate derivatives of this invention include any of the known caprolactone polyols that are commercially available, in the molecular weight range of 300 to 2000, and that are fully described, for example, in U.S. Pat. No. 3,169,945. As described in this patent the polycaprolactone polyols are produced by the catalytic polymerization of an excess of a caprolactone and an organic polyfunctional initiator having as least two reactive hydrogen atoms. The organic functional initiators can be any polyhydroxyl compound as is shown in U.S. Pat. No. 3,169,945. Illustrative thereof are the triols such as glycerol, trimethylolpropane, 1,2,6-hexanetriol, triethanolamine, triisopropanolamine, and the like; tetrols such as erythritol, pentaerythritol, N,N,N',N'-tetrakis(2-hydroxyethyl)ethylene diamine, and the like.

When the organic functional initiator is reacted with the caprolactone a reaction occurs that can be represented in its simplest form by the equation:

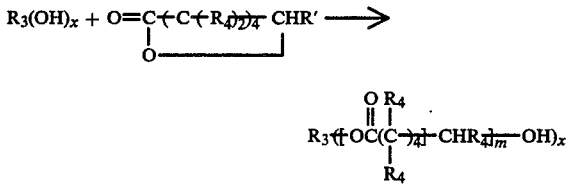

In this equation the organic functional initiator is the $R_3—(OH)_x$ compound and the caprolactone is the following compound:

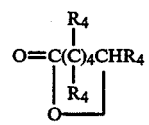

this can be caprolactone itself or a substituted caprolactone wherein $R_4$ is independently halogen, an alkyl, alkoxy, aryl, cycloalkyl, alkaryl or aralkyl group having up to twelve carbon atoms and wherein at least six of the R$_4$ groups are hydrogen atoms, as shown in U.S. Pat. No. 3,169,945. The polycaprolactone polyols that are used are shown by the formula on the right hand side of the equation; they can have an average molecular weight of from 200 to about 2,000. The preferred polycaprolactone polyol compounds are those having an average molecular weight of from about 300 to about 1000. The most preferred are the polycaprolactone triol and tetrol compounds having an average molecular weight of from about 300 to about 900; these are most preferred because of their low viscosity properties. In the formula m is an integer representing the average number of repeating units needed to produce the compound having said molecular weights. The hydroxyl number of the polycaprolactone polyol can be from about 15 to 600, preferably from 200 to 500; and the polycaprolactone polyol can have an average of from 3 to 6, preferably 3 tò 4, hydroxyl groups.

Illustrative of polycaprolactone polyols than can be used in this invention, one can mention the reaction products of a polyhydroxyl compound having an average from 3 to 6 hydroxyl groups with caprolactone. The manner in which these type polycaprolactone polyols is produced is shown in U.S. Pat. No. 3,169,945 and many such compositions are commercially available. In the following table there are listed illustrative polycaprolactone polyols. The first column lists the organic functional initiator that is reacted with the caprolactone and the average molecular weight of the polycaprolactone polyol is shown in the second column. Knowing the molecular weights of the initiator and of the polycaprolactone polyol one can readily determine the average number of molecules of caprolactone (CPL Units) that reacted to produce the compounds; this figure is shown in the third column.

| POLYCAPROLACTONE POLYOLS | | |
|---|---|---|
| Initiator | Average MW of polyol | Average No. of CPL units in molecules |
| 1  1,2,6-Hexanetriol | 476 | 3 |
| 2  Trimethylolethane | 577 | 4 |
| 3  Trimethylolpropane | 590 | 4 |
| 4  Trimetbylolpropane | 750 | 5.4 |
| 5  Trimethylolpropane | 1,103 | 8.5 |
| 6  Triethanolamine | 890 | 6.5 |
| 7  Erythritol 920 | 920 | 7 |
| 8  Pentaerythritol | 1,219 | 9.5 |
| 9  Dipentaerythritol | 938 | 6 |
| 10 Fructose 865 | 865 | 6 |

The structures of the compounds in the above tabulation are obvious to one skilled in the art based on the information given.

Polycaprolactone hexols can be prepared from the addition of caprolactone monomer to hexafunctional starters such as dipentaerythritol.

The polyfunctional acrylate derivative may be prepared by reacting the caprolactone polyol with acrylic or methacrylic acid in the presence of a strong acid catalyst. The strong acid catalyst may be sulfuric, methane sulfonic, or p-toluene sulfonic acid, or ion exchange resins, and the like. The catalyst is used in amounts of from about 0.1 to about 5.0, preferably from about 0.5 to about 2.0 percent.

The reaction to prepare the polyfunctional acrylate monomer is carried out at a temperature of from about 60° to about 120° C., preferably from about 80° to about 105° C. The reaction may be carried out at atmospheric pressure, although higher or lower pressures may be used. The reaction is generally carried out in the presence of air (oxygen) to prevent polymerization of the acrylic function. Oxygen is generally sparged through the reaction during the course of the reaction. The reaction is carried out for a period of time until the theoretical water is removed or until no further water is produced. This period is generally from about 3 to about 8 hours.

The reaction is generally carried out in the presence of a solvent of the type which removes water formed during the reaction as an azeotrope. Among the suitable solvents which can be used are the hydrocarbons such as octane, heptane, hexane, benzene, toluene or the xylenes, etc.

The reaction is generally carried out in the presence of a suitable inhibitor or combination of inhibitors to prevent polymerization of the acrylic or methacrylic acid double bonds. These inhibitors include the monomethyl ether of hydroquinone, benzoquinone, phenothiazine, methylhydroquinone, methylene blue, 2,5-di-t-butylhydroquinone, hydroquinone, and other common free radical inhibitors known in the art. The level of inhibitor used is from about 50 parts per million to about 2.0 percent.

In the reaction, one hydroxyl equivalent of the caprolactone polyol is reacted with excess of acrylic acid or methacrylic acid to form the caprolactone polyol acrylate. A hydroxyl containing acrylated polyol can also be prepared by reacting an excess equivalent of polyol with acrylic acid.

The process of this invention may be carried out by adding the caprolactone polyol, and solvent and then adding the acrylic or methacrylic acid, inhibitor and catalyst to a reaction vessel and then heating this to the reflux temperature. During the reaction, oxygen (or air) is continually bubbled through the reaction. After the reaction is complete, the excess acid may be removed by, for example, neutralization by adding a strong base such as sodium or potassium hydroxide, or stripping it off by conventional techniques, or by an ion exchange resin. Excess water may be removed from the reaction by, for example, adding a conventional drying agent such as magnesium sulfate, or by the use of vacuum stripping which also removes the solvent. Air must be sparged into the reaction mixture during stripping.

The acrylic esters may also be produced by other methods such as transesterification or acid chloride reaction.

The polyfunctional acrylate monomer produced has a viscosity of from about 10 to about 2000 centipoise at 25° C.

Mixtures of the polyfunctional acrylate derivatives may be used herein. Also, the polyfunctional acrylate monomers, either alone or in combination, may be mixed with the acrylate-capped polycaprolactone compounds of formula (I) wherein x is 1 to 2.

EXAMPLES

The following examples serve to illustrate specific embodiments of this invention and it is not intended that the invention shall be limited by the examples.

The following designations used in the Examples and Controls have the following meaning:

Caprolactone polyol (I)—A trihydroxyfunctional polycaprolactone polyol with an average hydroxyl number of 310 and an average molecular weight of 540 (Tone-0305 obtained from Union Carbide Corporation).

Caprolactone polyol (II)—A trihydroxyfunctional polycaprolactone polyol with an average hydroxyl number of 187 and an average molecular weight of 900 (Tone-0310 obtained from Union Carbide Corporation).

Caprolactone polyol (III)—A tetrahydroxyfunctional polycaprolactone polyol produced by reacting pentaerythritol and caprolactone with an average hydroxyl number of 360 and an average molecular weight of 622.

Caprolactone polyol (IV)—A trihydroxyfunctional polycaprolactone polyol with an average hydroxyl number of 560 and an average molecular weight of 300 (Tone -301 obtained from Union Carbide Corporation).

EXAMPLE 1

A 2000 ml glass reaction flask was equipped with a stirrer, thermometer and condenser, Dean-Stark trap, air inlet and heating mantle and used an the reaction vessel. 300 grams of Caprolactone polyol (I), 147.3 g. of glacial acrylic acid, 600 ml. of benzone, 5 ml. of concentrated sulfuric acid and 4 g. of hydroquinone were added to the reaction flask at room temperature. The contents of the flask were then heated to about 85° C. over a period of one hour and maintained at reflux at atmospheric pressure until no further water was produced (about 4.5 hours). During the reaction, air was continually bubbled through the reaction. The reaction mixture was cooled to about 60° C. in a separatory funnel and about 50 ml of benzene added. Then, about 200 g of a 15 percent aqueous sodium hydroxide solution was dripped through the separatory funnel. A second aliquot of 200 g of a 15 percent aqueous sodium hydroxide solution was added and then the contents shaken. Excess acid and hydroquinone inhibitor were washed out by shaking the solution three times with 50 g of a 15 percent aqueous sodium hydroxide solution. After the contents settled, 10 g of magnesium sulfate were added while stirring to remove any remaining water, then the contents filtered to remove the magnesium sulfate. 100 parts per million of mono methyl ether of hydroquinone based on the final product was added and the contents were then stripped of solvent using an air bleed. A 60 to 70% yield was obtained. The product had a viscosity of 250 centipoise at room temperature.

EXAMPLE 2

The procedure of Example 1 was repeated except that the reaction flask was charged with the following:
300 g: Caprolactone polyol (II)
88.4 g: Glacial acrylic acid
150 ml: Benzene
5 g: Hydroquinone
3 ml: Concentrated sulfuric acid The product had a viscosity of 442 centipoise at room temperature.

EXAMPLE 3

The procedure of Example 1 was repeated except that the reaction flask was charged with the following:
311 g: Caprolactone polyol (III)
174 g: Glacial acrylic acid
600 ml: Benzene
1 g: Hydroquinone
2 ml: Concentrated sulfuric acid The product had a viscosity of 624 centipoise at room temperature.

EXAMPLE 4

The procedure of Example 1 was repeated except that air was not used and the reaction flask was charged with the following:
150 g: Caprolactone polyol (IV)
155 g: Methacrylic acid
300 ml: Heptane
0.05 g: Methylene blue
5 ml: Concentrated sulfuric acid The product had a viscosity of 50 centipoise at room temperature.

What is claimed is:

1. A process for the preparation of polyfunctional acrylate derivatives of caprolactone-polyols characterized by the structural formula:

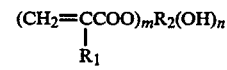

wherein $R_1$ is hydrogen or methyl, $R_2$ is the residue of a caprolactone-polyol, m is an integer of 2 to 6, and n is an integer of 0 to 2, with the proviso that m+n is greater than or equal to 3 and m is greater than n, comprising the steps of:
 (a) reacting acrylic acid or methacrylic acid with a caprolactone-polyol for a period of from about 3 to 8 hours at a temperature of from about 60° to 120° C. in the presence of from about 0.1 to about 5% by weight of a strong acid catalyst, and from 50 parts per million to about 2% by weight of a polymerization inhibitor for the acrylic or methacrylic acid, said reacting being conducted with simultaneous sparging of air or oxygen through the reaction mixture to produce a reaction product comprising said polyfunctional acrylate derivative;
 (b) vacuum stripping said reaction product comprising said polyfunctional acrylate derivative, while sparging said air or oxygen therethrough; and
 (c) recovering said polyfunctional acrylate derivative.

2. The process of claim 1, wherein said polyfunctional acrylate derivative is prepared by reacting acrylic acid with a caprolactone-polyol prepared from epsilon-caprolactone and trimethylolpropane.

3. The process of claim 1, wherein said polyfunctional acrylate derivative is prepared by reacting acrylic acid with a caprolactone-polyol prepared from epsilon-caprolactone and pentaerythritol.

4. The process of claim 3, wherein step (a) is carried out in the presence of a solvent which removes water formed during the reaction as an azeotrope.

5. The process of claim 4, further comprising the step of neutralizing residual acrylic or methacrylic acid present in the reaction product comprising said polyfunctional acrylate derivative prior to vacuum stripping.

* * * * *